United States Patent
Inui et al.

(10) Patent No.: US 10,265,522 B2
(45) Date of Patent: Apr. 23, 2019

(54) ELECTRO-STIMULATOR

(71) Applicant: Panasonic Intellectual Property Management Co., Ltd., Osaka (JP)

(72) Inventors: Keita Inui, Shiga (JP); Izumi Mihara, Osaka (JP); Ryo Ichimura, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 62 days.

(21) Appl. No.: 15/528,518

(22) PCT Filed: Nov. 17, 2015

(86) PCT No.: PCT/JP2015/005722
§ 371 (c)(1),
(2) Date: May 22, 2017

(87) PCT Pub. No.: WO2016/088311
PCT Pub. Date: Jun. 9, 2016

(65) Prior Publication Data
US 2017/0266441 A1     Sep. 21, 2017

(30) Foreign Application Priority Data

Dec. 5, 2014   (JP) ................................ 2014-247423

(51) Int. Cl.
*A61N 1/00*   (2006.01)
*A61N 1/36*   (2006.01)
(Continued)

(52) U.S. Cl.
CPC ........ *A61N 1/36014* (2013.01); *A61B 5/1116* (2013.01); *A61B 5/1123* (2013.01);
(Continued)

(58) Field of Classification Search
CPC ....... A61B 5/1116; A61B 5/1123; A61N 1/08; A61N 1/22; A61N 1/321; A61N 1/36003; A61N 1/36014
See application file for complete search history.

(56) References Cited

U.S. PATENT DOCUMENTS

| | | | |
|---|---|---|---|
| 5,919,149 A | * | 7/1999 | Allum ................... A61B 5/1116 600/595 |
| 2008/0147143 A1 | | 6/2008 | Popovic et al. |

(Continued)

FOREIGN PATENT DOCUMENTS

| | | |
|---|---|---|
| JP | 2009-136585 | 6/2009 |
| JP | 2012-011102 | 1/2012 |
| WO | 2013/069004 | 5/2013 |

OTHER PUBLICATIONS

The Extended European Search Report dated Nov. 3, 2017 for the related European Patent Application No. 15864763.6.
(Continued)

*Primary Examiner* — George Manuel
(74) *Attorney, Agent, or Firm* — McDermott Will & Emery LLP

(57) ABSTRACT

Electro-stimulator (1) includes electrode pad (60) that outputs current to provide electrical stimulation to a muscle, angular velocity sensor (51) that detects information on motion of a waist, and controller (30) that adjusts magnitude of the current output from electrode pad (60) based on a result of the detection by angular velocity sensor (51). Electro-stimulator (1) further includes belt (11) that supports electrode pad (60), angular velocity sensor (51), and controller (30). Thus, current flows through an abdomen, thereby providing electrical stimulation to the abdomen, and enabling proper training of abdominal muscles.

6 Claims, 7 Drawing Sheets

(51) Int. Cl.
    *A61B 5/11*     (2006.01)
    *A61N 1/08*     (2006.01)
    *A61N 1/22*     (2006.01)
    *A61N 1/32*     (2006.01)

(52) U.S. Cl.
    CPC ............... *A61N 1/08* (2013.01); *A61N 1/22* (2013.01); *A61N 1/321* (2013.01); *A61N 1/36003* (2013.01)

(56) References Cited

U.S. PATENT DOCUMENTS

| | | |
|---|---|---|
| 2009/0240305 A1 | 9/2009 | Lee et al. |
| 2011/0060215 A1* | 3/2011 | Tupin, Jr. ............. A61B 5/0507 600/425 |
| 2014/0303680 A1 | 10/2014 | Donnelly et al. |
| 2014/0358193 A1 | 12/2014 | Lyons et al. |
| 2016/0331974 A1 | 11/2016 | Lyons et al. |

OTHER PUBLICATIONS

International Search Report of PCT application No. PCT/JP2015/005722 dated Jan. 26, 2016.

* cited by examiner

ELECTRO-STIMULATOR

TECHNICAL FIELD

The present disclosure relates to an electro-stimulator for providing electrical stimulation to muscles.

BACKGROUND ART

Electro-stimulators for providing electrical stimulation to muscles are known. An example is an electro-stimulator in Patent Literature 1 that includes electrodes for outputting current, sensors for detecting information on motion of a knee joint, and a supporter to which the electrodes and the sensors are attached, to be worn around a lower limb. This electro-stimulator adjusts magnitude of current output from the electrodes according to results of detection by the sensors.

By the above-described electro-stimulator, abdominal muscles cannot be trained properly.

CITATION LIST

Patent Literature

PTL 1: Unexamined Japanese Patent Publication No. 2012-11102

SUMMARY OF THE INVENTION

An object of the present disclosure is to provide an electro-stimulator that enables proper training of abdominal muscles.

An electro-stimulator according to one form of the present disclosure is an electro-stimulator for providing electrical stimulation to muscles. The electro-stimulator includes an electrode pad that outputs current to provide electrical stimulation, a sensor that detects information on motion of a waist, a controller that adjusts magnitude of the current output from the electrode pad based on a result of the detection by the sensor, and a belt that supports the electrode pad, the sensor, and the controller.

The above-described electro-stimulator enables proper training of abdominal muscles.

Figure 1:
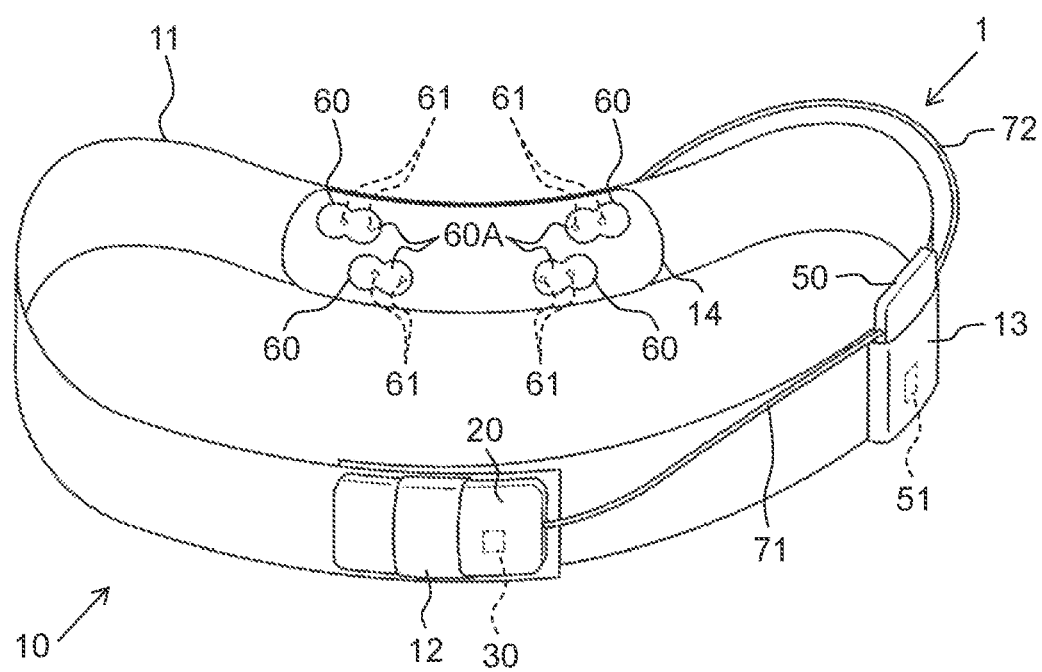
FIG. 1 is a perspective view of an electro-stimulator in an exemplary embodiment.

DESCRIPTION OF EMBODIMENT (One Form of Electro-Stimulator)

[1] An electro-stimulator according to the present disclosure is an electro-stimulator for providing electrical stimulation to a muscle, and includes an electrode pad that outputs current to provide the electrical stimulation, a sensor that detects information on motion of a waist, a controller that adjusts magnitude of the current output from the electrode pad based on a result of the detection by the sensor, and a belt that supports the electrode pad, the sensor, and the controller.

This electro-stimulator allows a user to wear the belt on the waist so that the electrode pad is disposed around the abdomen. When the user wearing the belt moves the waist, the sensor detects information on the motion of the waist. Based on the result of the detection by the sensor, the controller causes the electrode pad to output current. Consequently, the current flows through the abdomen, thereby providing electrical stimulation to the abdomen, and enabling proper training of an abdominal muscle.

[2] According to an example of the electro-stimulator, the information on the motion of the waist includes angular velocity of the waist.

The motion of the waist causes abdominal muscles to move. Thus, the angular velocity of the waist has a correlation with the motion of the abdominal muscles. Based on this, the sensor of the electro-stimulator in [2] described above detects the angular velocity of the waist. Consequently, electrical stimulation is more likely to be provided properly to the abdomen, according to the motion of the abdominal muscles.

[3] According to an example of the electro-stimulator, the sensor detects the information on the motion of the waist that accompanies motion of a body.

When electrical stimulation is provided to moving abdominal muscles, a higher training effect is likely to be obtained than when electrical stimulation is provided to motionless abdominal muscles. Based on this, the sensor of the electro-stimulator in [3] described above detects information on the motion of the waist. This increases a possibility that the abdominal muscles are trained efficiently.

[4] According to an example of the electro-stimulator, the motion of the body is one of walking motion, running motion, twisting motion, and bending motion.

The mode of motion of the abdominal muscles differs according to the type of motion of the body. Based on this, the sensor of the electro-stimulator in [4] described above detects the information on the motion of the waist according to the type of motion of the body. Consequently, electrical stimulation according to the mode of motion of the abdominal muscles is more likely to be provided to the abdomen.

[5] According to an example of the electro-stimulator, the controller adjusts the magnitude of the current output from the electrode pad, based on a current output form set for each type of motion of the body and the result of the detection by the sensor.

This electro-stimulator provides electrical stimulation to the abdomen according to the motion of the abdominal muscles. This further increases the possibility that the abdominal muscles are trained efficiently. Further, this reduces a fear that undesirable electrical stimulation is provided to the abdomen.

[6] According to an example of the electro-stimulator, when a value of the angular velocity reflecting the result of the detection by the sensor falls within a predetermined range, the controller prevents the electrode pad from outputting current, or makes the current output from the electrode pad smaller than current to be output when the value of the angular velocity deviates from the predetermined range.

The value of the angular velocity correlates with a degree of motion of the waist. Thus, by the predetermined range being preset in association with the motion of the waist, the relationship between the value of the angular velocity and the predetermined range implies the motion of the waist. According to an example, when the value of the angular velocity falls within the predetermined range, it is implied that the motion of the waist is small or the waist is not moving. When the abdominal muscles are not moving or the motion of the abdominal muscles is small, current passed from the electrode pad through an abdominal muscle may not train the abdominal muscle efficiently. Based on this, the controller of the electro-stimulator in [6] described above adjusts the current. This further increases the possibility that the abdominal muscles are trained efficiently.

[7] According to an example of the electro-stimulator, when a duration, during which a state where the value of the angular velocity deviates from the predetermined range continues, is more than or equal to a predetermined time, the controller prevents the electrode pad from outputting current, or makes the current output from the electrode pad smaller than current to be output when the duration is less than the predetermined time.

When the body moves for training, a state where the value of the angular velocity falls within the predetermined range, and the state where the value of the angular velocity deviates from the predetermined range are repeated substantially periodically. On the other hand, when an abnormality occurs in output of the sensor, the state where the value of the angular velocity deviates from the predetermined range may continue. Thus, when the duration is more than or equal to the predetermined time, it is highly likely that an abnormality in the output of the sensor has actually occurred. Based on this, the controller of the electro-stimulator in [7] described above adjusts the current. This reduces a fear that the current is adjusted based on the value of the angular velocity that may not reflect the actual motion of the waist.

Exemplary Embodiment

FIG. 1 illustrates an example of belt-type electro-stimulator 1 that is wearable on a target region. Electro-stimulator 1 includes wearing part 10 wearable around an abdomen, which is an example of the target region, main body 20 including some components of electro-stimulator 1, and a plurality of electrode pads 60 that output current to provide electrical stimulation to the target region. The number of electrode pads 60 is four, for example.

Electro-stimulator 1 further includes controller 30 that controls electrode pads 60, angular velocity sensor 51, which is an example of a sensor that detects information on motion of a waist, and sensor case 50 housing angular velocity sensor 51. Controller 30 is housed within main body 20. Electro-stimulator 1 further includes main cord 71 that connects controller 30 and angular velocity sensor 51 via sensor case 50, and electrode cord 72 that connects the plurality of electrode pads 60 and sensor case 50. Main cord 71 and electrode cord 72 are electrically connected within sensor case 50. Consequently, controller 30 and the plurality of electrode pads 60 are electrically connected via cords 71, 72.

Wearing part 10 includes belt 11 to be wrapped around the target region, main body holder 12 that holds main body 20, sensor holder 13 that holds sensor case 50, and pad holder 14 that holds electrode pads 60. Belt 11 is formed of a stretchable material, for example. A hook and a loop (not shown) of a hook-and-loop fastener are attached to both longitudinal end portions of belt 11. By wrapping belt 11 around the target region and joining the hook and the loop of the hook-and-loop fastener together, belt 11 is worn around the target region. Belt 11 has hole 11A through which electrode cord 72 is inserted.

An example of main body holder 12 is a loop capable of holding main body 20, formed at one longitudinal end portion of belt 11. By inserting main body 20 into main body holder 12, main body 20 and controller 30 are supported by belt 11.

An example of sensor holder 13 is a loop capable of holding sensor case 50, formed between main body holder 12 and pad holder 14 in a longitudinal direction of belt 11. By inserting sensor case 50 into sensor holder 13, sensor case 50 and angular velocity sensor 51 are supported by belt 11.

An example of pad holder 14 is a thick sheet having a structure for detachably attaching electrode pads 60, formed on an inside of a longitudinally intermediate portion of belt 11. By attaching electrode pads 60 to pad holder 14, electrode pads 60 are supported by belt 11. Pad holder 14 has eight holes 14A into which terminals 73 of electrode cord 72 are inserted.

An example of electrode pad 60 is a thin film pad having conductivity. A shape of electrode pad 60 is a symmetrical gourd shape in which a constriction is formed. Two electrode pads 60 are attached to a right-side portion of pad holder 14. Two electrode pads 60 are attached to a left-side portion of pad holder 14.

Figure 2:
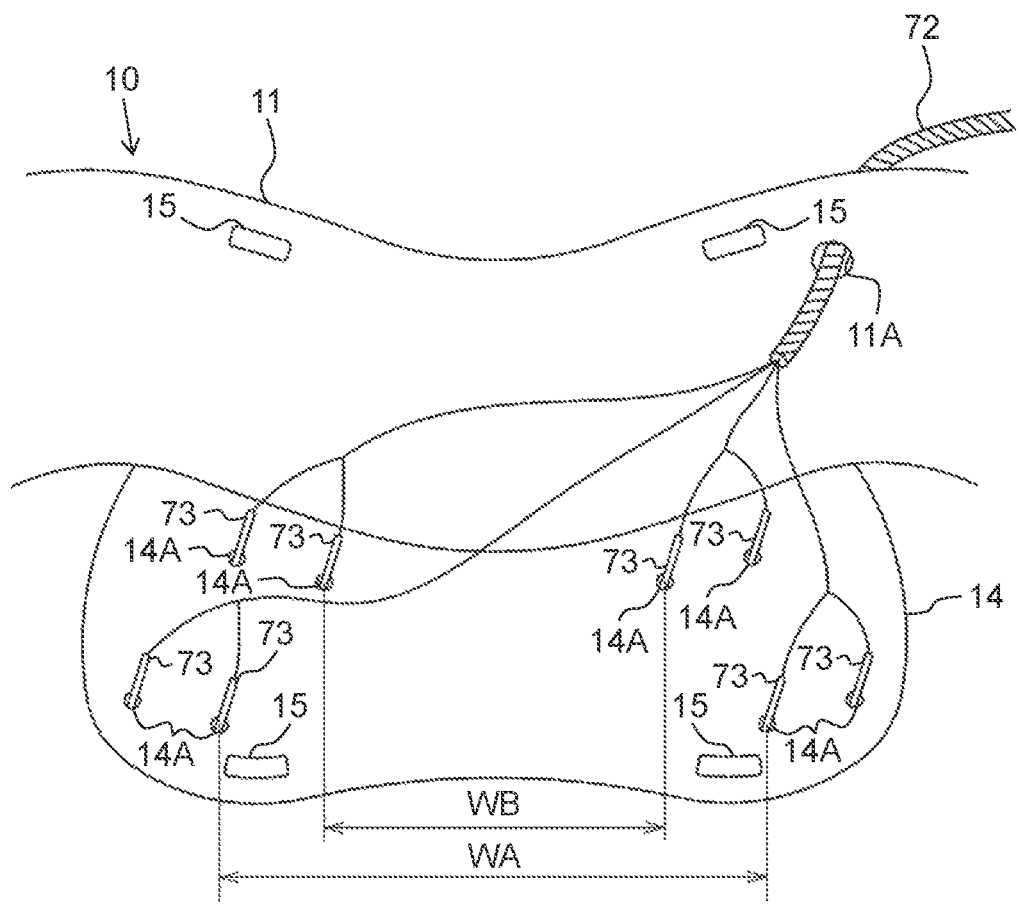
FIG. 2 is a developed view of a pad holder in FIG. 1.

Main cord 71 and electrode cord 72 are laid along an outer periphery of belt 11. Electrode cord 72 is a single cord in which eight cords are bundled, for example. Terminals 73 are attached to respective front ends of the eight cords. As illustrated in FIG. 2, electrode cord 72 is inserted through hole 11A of belt 11, and terminals 73 are inserted through holes 14A of pad holder 14. Thus, terminals 73 are exposed to an outside of pad holder 14.

FIG. 2 illustrates a plan view of belt 11 with pad holder 14 developed. Pad holder 14 is connected to an edge of belt 11. By folding pad holder 14 back to belt 11 and joining hook-and-loop fasteners 15 formed on an inner surface of pad holder 14 and an inner surface of belt 11 together, pad holder 14 is retained by belt 11. In this state, electrode cord 72 is housed in a space formed between the inner surface of belt 11 and the inner surface of pad holder 14.

Four holes 14A formed on a hook-and-loop fastener 15 side of pad holder 14 are arranged substantially in a row. Four holes 14A formed on a side of connection of pad holder 14 with belt 11 are likewise arranged substantially in a row. Space WA between two holes 14A formed on a longitudinally central side of pad holder 14 in the row on the hook-and-loop fastener 15 side is wider than space WB between two holes 14A formed on a longitudinally central side of pad holder 14 in the row on the connection side of pad holder 14. Respective sizes of space WA and space WB and a relationship between space WA and space WB are determined based on a standard shape of abdominal muscles, for example.

Figure 3:
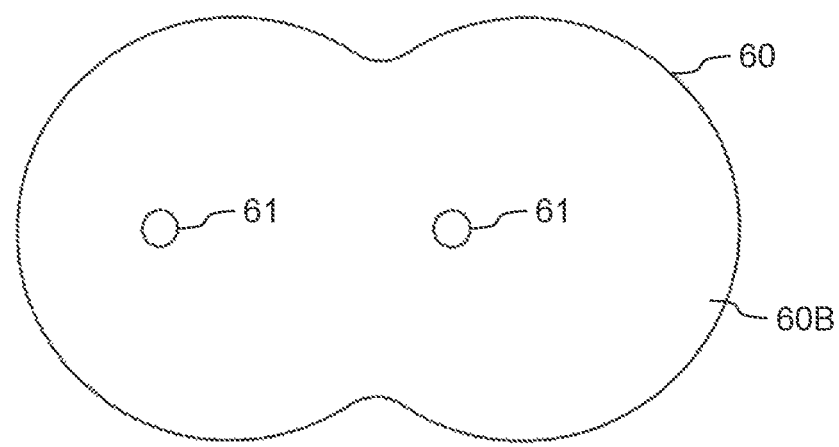
FIG. 3 is a front view of a pad in FIG. 1.

FIG. 3 illustrates electrode pad 60 detached from pad holder 14. Electrode pad 60 has attached surface 60A (see FIG. 1), which is a surface attached to the target region, non-attached surface 60B, which is a surface facing pad holder 14 (see FIG. 2), and two hooks 61 to which terminals 73 (see FIG. 2) of electrode cord 72 (see FIG. 2) are connected. Attached surface 60A is coated with a gel material having conductivity and adhesion. Hooks 61 are mounted on non-attached surface 60B. Positions of hooks 61 on electrode pad 60 are determined such that a center between two hooks 61 in a longitudinal direction of electrode pad 60 is longitudinally offset with respect to a longitudinal center of the electrode pad 60.

By attaching hooks 61 to terminals 73 exposed from holes 14A of pad holder 14 (see FIG. 2), electrode pads 60 are held by pad holder 14. In this state, electrode cord 72, terminals 73, hooks 61, and attached surfaces 60A are electrically connected.

Figure 4:
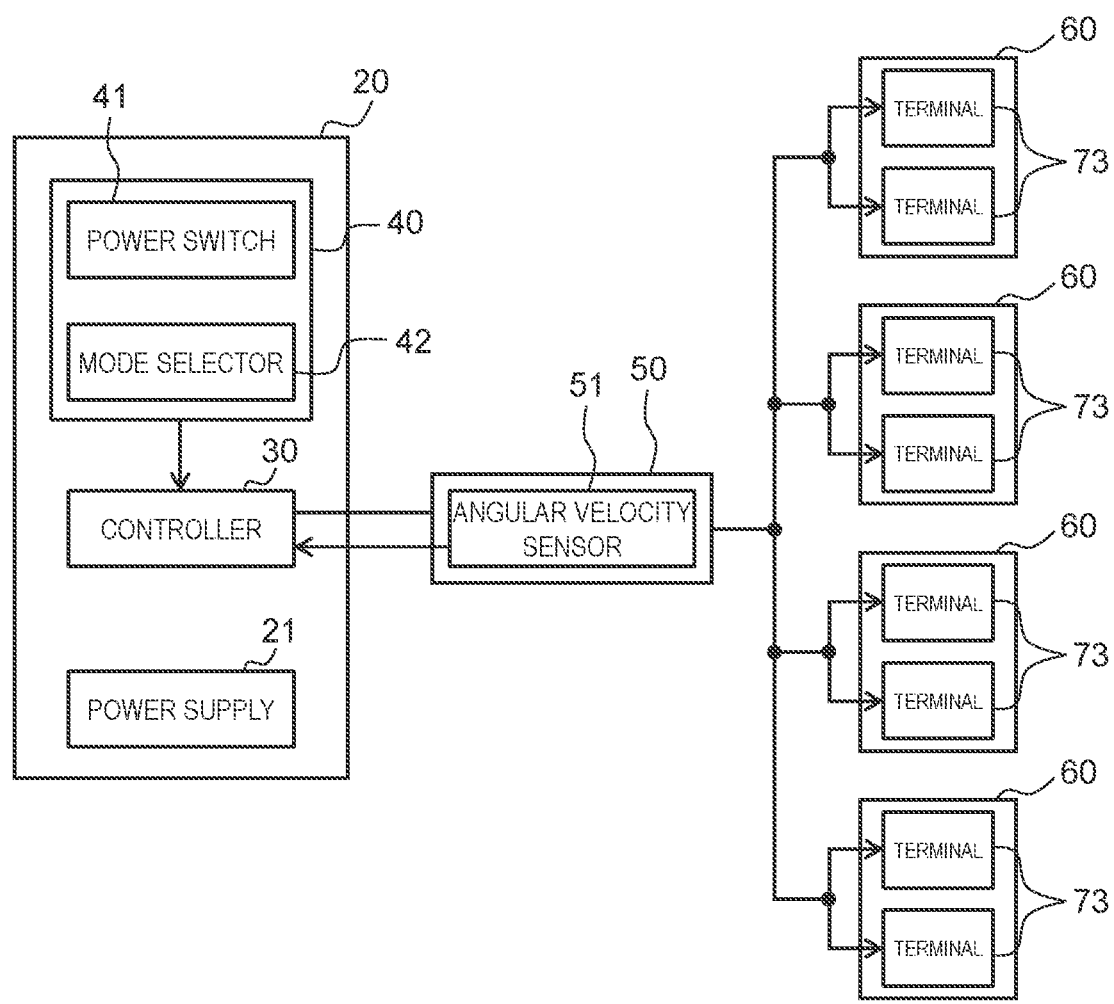
FIG. 4 is a block diagram of the electro-stimulator in FIG. 1.

FIG. 4 illustrates a block diagram of main body 20. Main body 20 includes, in addition to controller 30, power supply 21 that supplies power of a primary battery or a secondary battery to controller 30, electrode pads 60, and others, and operating unit 40 operated to select an operation of electro-stimulator 1. Operating unit 40 has power switch 41 for switching power of electro-stimulator 1 on and off, and mode selector 42 for selecting a form of current output by electrode pads 60.

Mode selector 42 has the following four types of buttons, for example. A first button is a button for selecting a walking motion mode, which is suitable for walking motion. A second button is a button for selecting a running motion mode, which is suitable for running motion. A third button is a button for selecting a twisting motion mode, which is suitable for twisting motion. A fourth button is a button for selecting a bending motion mode, which is suitable for bending motion.

Controller 30 previously stores various types of information to be referred to for controlling electrode pads 60. An example is a plurality of current output forms corresponding to the motion modes selected by mode selector 42, and a plurality of thresholds defining predetermined ranges to be compared with a value of angular velocity obtained from a result of detection by angular velocity sensor 51.

Angular velocity sensor 51 detects angular velocity of a waist that accompanies motion of a body. The motion of the body is, for example, one of walking motion, running motion, twisting motion, and bending motion. For example, angular velocity around a first axis, an axis along a direction of the height of a human body, and around a second axis, an axis along a side to side direction of a human body, is detected by angular velocity sensor 51.

When one motion mode of the walking motion mode, the running motion mode, and the twisting motion mode is selected by mode selector 42, the angular velocity around the first axis is detected by angular velocity sensor 51. When the bending motion mode is selected by mode selector 42, the angular velocity around the second axis is detected by angular velocity sensor 51. Angular velocity sensor 51 detects the angular velocity around the first axis or the second axis every few microseconds, for example, and outputs a result of the detection to controller 30.

Controller 30 executes the following arithmetic processing, thereby calculating a value of the angular velocity from the result of the detection by angular velocity sensor 51. First, moving average processing is executed. This processing causes a digitized result of detection by angular velocity sensor 51 to be passed through a low-pass filter so that certain high-frequency signals are removed from the result of the detection by angular velocity sensor 51, and a sinusoidal signal is generated. Next, a value of the angular velocity is determined based on the sinusoidal signal.

Figure 5:
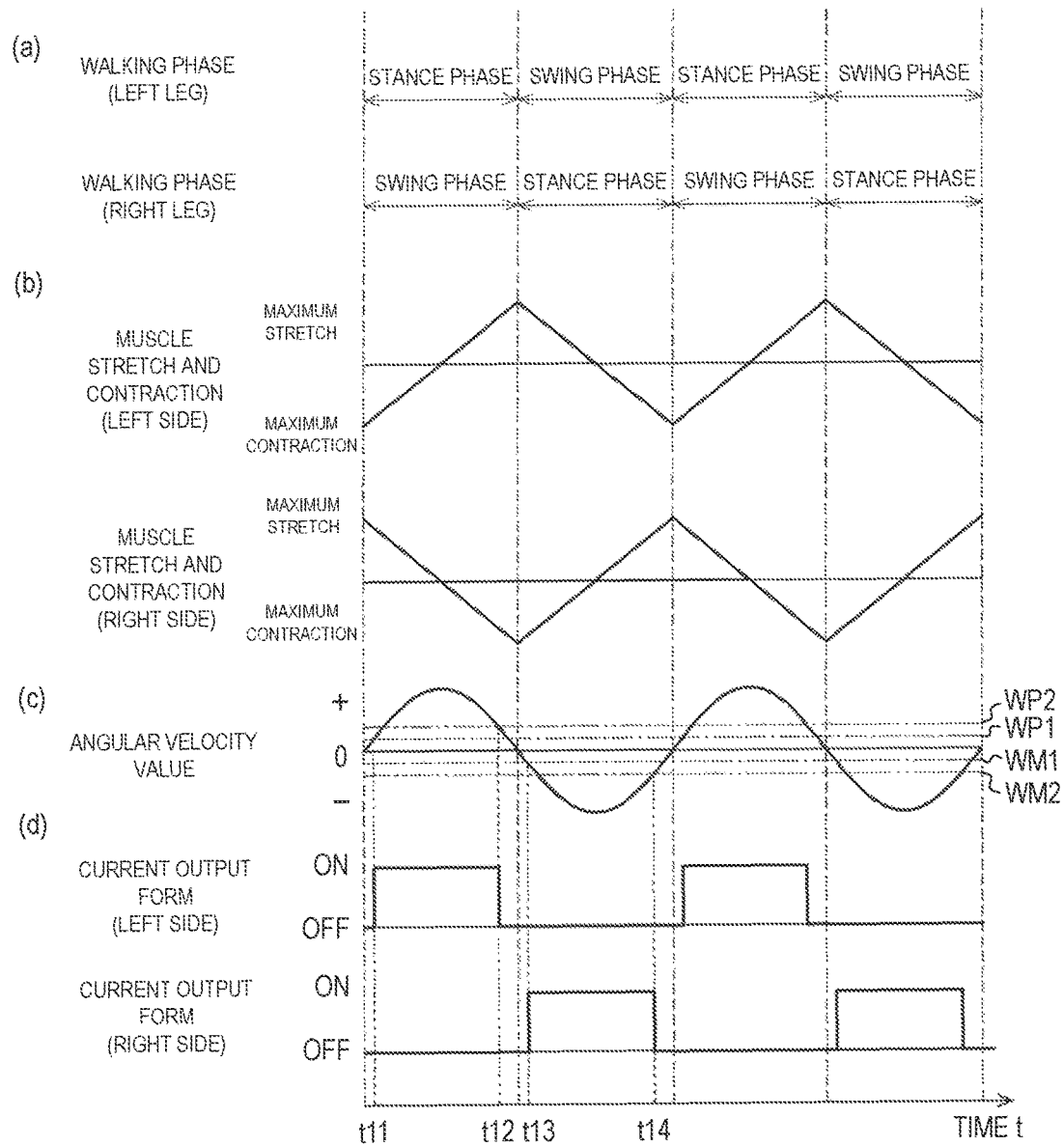
FIG. 5 is a time chart illustrating an example of changes in each item during walking motion of the electro-stimulator in FIG. 1 (in which (a) represents walking phases, (b) represents muscle stretch and contraction, (c) represents an angular velocity value, and (d) represents current output forms).

With reference to FIG. 5, an example of the current output forms in the walking motion mode will be described.

FIG. 5(a) illustrates walking phases of legs in walking motion. One cycle of walking motion is divided into two walking phases, a stance phase and a swing phase. The stance phase is a period during which at least a part of the foot contacts the ground, a floor, or the like. The swing phase is a period during which the foot is off the ground, a floor, or the like.

FIG. 5(b) illustrates moving states of abdominal muscles. When the walking phase of the left leg is the stance phase and the walking phase of the right leg is the swing phase, a trunk rotates to the right around the first axis, thereby stretching left-side abdominal muscles contained in a left side of a body, and contracting right-side abdominal muscles contained in a right side of the body. Between a time when the walking phase of the right leg shifts from the swing phase to the stance phase and a time when the walking phase of the left leg shifts from the stance phase to the swing phase, the left-side abdominal muscles stretch most in the walking motion, and the right-side abdominal muscles contract most in the walking motion. In this case, the right-side abdominal muscles act as agonist muscles, and the left-side abdominal muscles act as antagonist muscles.

When the walking phase of the left leg is the swing phase and the walking phase of the right leg is the stance phase, the trunk rotates to the left around the first axis, thereby contracting the left-side abdominal muscles and stretching the right-side abdominal muscles. Between a time when the walking phase of the left leg shifts from the swing phase to the stance phase and a time when the walking phase of the right leg shifts from the stance phase to the swing phase, the left-side abdominal muscles contract most in the walking motion, and the right-side abdominal muscles stretch most in the walking motion. In this case, the left-side abdominal muscles act as agonist muscles, and the right-side abdominal muscles act as antagonist muscles.

FIG. 5(c) illustrates the value of the angular velocity determined from results of detection by angular velocity sensor 51.

When user 100 forms walking motion, angular velocity sensor 51 detects the angular velocity around the first axis. For example, when a pelvis rotates to the left around the first axis, the angular velocity indicates positive values, and when the pelvis rotates to the right around the first axis, the angular velocity indicates negative values.

In walking motion, the trunk and the pelvis rotate in directions opposite to each other around the first axis. By considering this point, the stretching and contracting states of the abdominal muscles can be determined properly from results of detection by angular velocity sensor 51. When abdominal muscles on one of the right side and the left side stretch most, or when walking motion is stopped, the angular velocity indicates substantially zero. The angular velocity being substantially zero is determined by the angular velocity indicating a magnitude of less than a predetermined angular velocity, for example.

Examples of the thresholds referred to in the walking motion mode are the following four types. The first is first threshold WP1, which is a threshold referred to for flowing current through left-side abdominal muscles. The second is second threshold WP2, which is a threshold referred to for stopping the flow of the current. The third is third threshold WM1, which is a threshold referred to for flowing current through right-side abdominal muscles. The fourth is fourth threshold WM2, which is a threshold referred to for stopping the flow of the current. The above-described thresholds are set by considering response delay between the output of a command signal from controller 30 to electrode pads 60 and the reflection of the command in the actual operation of electrode pads 60. Thus, thresholds WP1, WM1 referred to for flowing current and thresholds WP2, WM2 referred to for stopping current flow have different values.

Controller 30 compares the value of the angular velocity reflecting a result of detection by angular velocity sensor 51 with the thresholds to determine whether the value of the angular velocity falls within a predetermined range. For example, two types of predetermined ranges are set for the walking motion mode. The first is a first predetermined range that is compared with the value of the angular velocity when the value of the angular velocity is changing from a negative peak to a positive peak. The second is a second predetermined range that is compared with the value of the angular velocity when the value of the angular velocity is changing from the positive peak to the negative peak. The first predetermined range and the second predetermined range are set across a positive region and a negative region as below, for example.

The first predetermined range is defined by first threshold WP1 and fourth threshold WM2. A range defined by first threshold WP1 and zero is a portion present in the positive region within the first predetermined range. A range defined by fourth threshold WM2 and zero is a portion present in the negative region within the first predetermined range.

The second predetermined range is defined by second threshold WP2 and third threshold WM1. A range defined by second threshold WP2 and zero is a portion present in the positive region within the second predetermined range. A range defined by third threshold WM1 and zero is a portion present in the negative region within the second predetermined range.

Controller 30 adjusts current output from electrode pads 60, based on a relationship between the value of the angular velocity and the thresholds, and a motion mode selected by mode selector 42. For example, controller 30 determines the timing of outputting and stopping current based on the relationship between the value of the angular velocity and the thresholds.

When the number of times when the same determination result on the relationship between the value of the angular velocity and the thresholds is successively obtained is more than or equal to a predetermined number of times, controller 30 determines that the determination result is valid, and uses the determination result for the control of electrode pads 60. On the other hand, when the number of times when the same determination result on the relationship between the value of the angular velocity and the thresholds is successively obtained is less than the predetermined number of times, controller 30 determines that the determination result is invalid, and does not use the determination result at that point of time for the control of electrode pads 60. The predetermined number of times is set for each motion mode.

FIG. 5(d) illustrates current output forms.

When the value of the angular velocity changes from a magnitude of less than first threshold WP1 to a magnitude of more than or equal to first threshold WP1 at time t11, controller 30 causes left-side electrode pads 60 to output current, based on a result of comparison between the value of the angular velocity and first threshold WP1. In this case, since the value of the angular velocity is more than or equal to first threshold WP1, it is implied that left-side abdominal muscles are stretching as antagonist muscles. Thus, controller 30 causes left-side electrode pads 60 to output current so that electrical stimulation is provided to the left-side abdominal muscles.

When the value of the angular velocity changes from a magnitude of more than or equal to second threshold WP2 to a magnitude of less than second threshold WP2 at time t12, controller 30 stops the output of the current by left-side electrode pads 60, based on a result of comparison between the value of the angular velocity and second threshold WP2. In this case, since the value of the angular velocity is less than second threshold WP2, it is implied that the moving speed of the abdominal muscles is low, or the abdominal muscles are not moving. Thus, controller 30 stops the output of the current by left-side electrode pads 60 so that no electrical stimulation is provided to the abdominal muscles.

When the value of the angular velocity changes from a magnitude of more than or equal to third threshold WM1 to a magnitude of less than third threshold WM1 at time t13, controller 30 causes right-side electrode pads 60 to output current, based on a result of comparison between the value of the angular velocity and third threshold WM1. In this case, since the value of the angular velocity is less than third threshold WM1, it is implied that right-side abdominal muscles are stretching as antagonist muscles. Thus, controller 30 causes right-side electrode pads 60 to output current so that electrical stimulation is provided to the right-side abdominal muscles.

When the value of the angular velocity changes from a magnitude of less than fourth threshold WM2 to a magnitude of more than or equal to fourth threshold WM2 at time t14, controller 30 stops the output of the current by right-side electrode pads 60, based on a result of comparison between the value of the angular velocity and fourth threshold WM2. In this case, since the value of the angular velocity is more than or equal to fourth threshold WM2, it is implied that the moving speed of the abdominal muscles is low, or the abdominal muscles are not moving. Thus, controller 30 stops the output of the current by right-side electrode pads 60 so that no electrical stimulation is provided to the abdominal muscles.

In this manner, controller 30 stops the output of current by electrode pads 60 when the value of the angular velocity falls within the predetermined ranges, and causes corresponding electrode pads 60 to output current when the value of the angular velocity deviates from the predetermined ranges. When the walking motion is continued at and after time t14, controller 30 repeatedly executes the same processing as the processing executed at times t11 to t14. When running motion is formed in place of walking motion, controller 30 executes the same processing as the processing executed when walking motion is formed.

Figure 6:
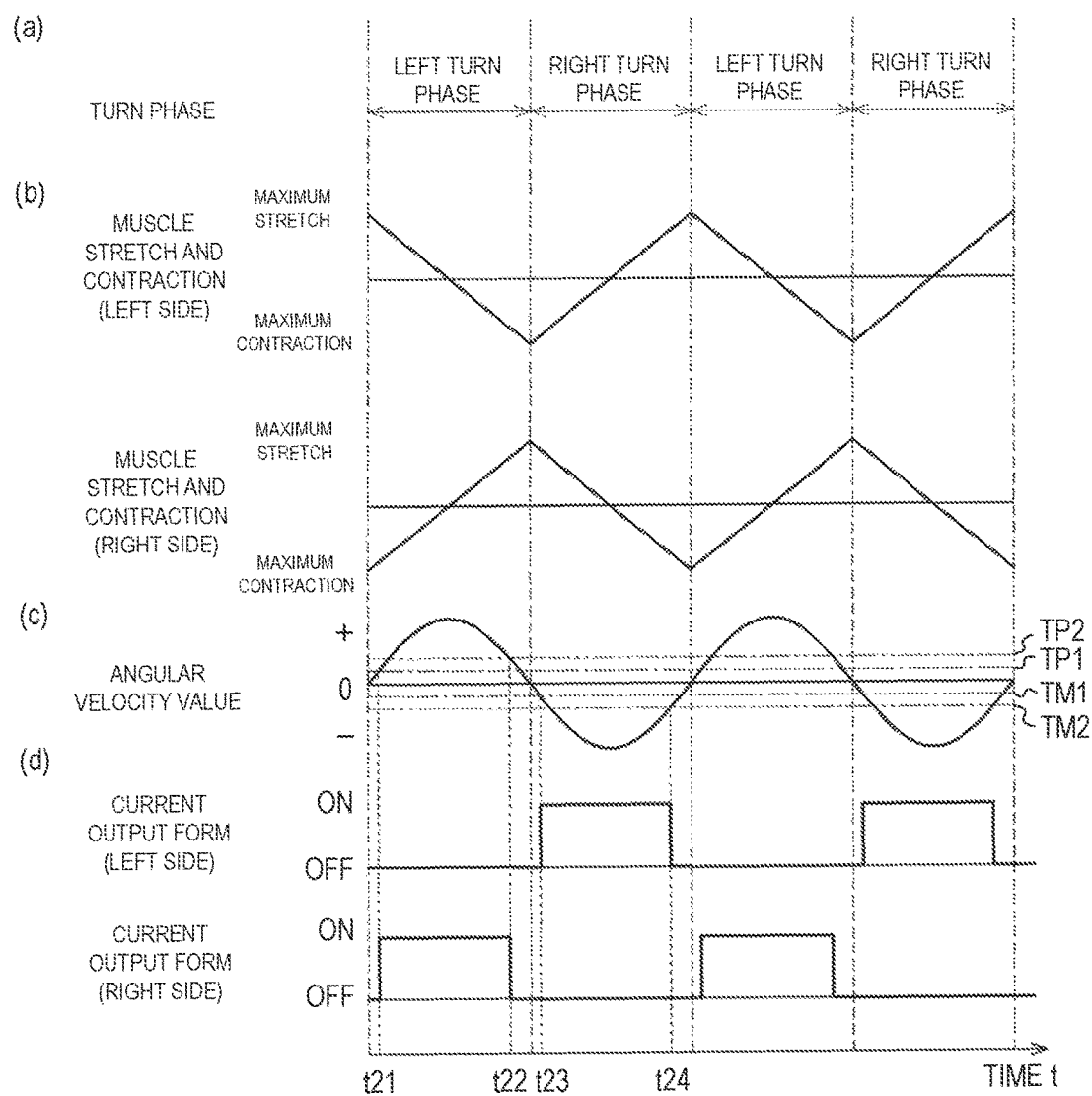
FIG. 6 is a time chart illustrating an example of changes in each item during twisting motion of the electro-stimulator in FIG. 1 (in which (a) represents a turn phase, (b) represents muscle stretch and contraction, (c) represents an angular velocity value, and (d) represents current output forms).

With reference to FIG. 6, an example of the current output forms in the twisting motion mode will be described.

FIG. 6(a) illustrates a turn phase in twisting motion. One cycle of twisting motion is divided into two turn phases, which are a left turn phase and a right turn phase. The left turn phase represents a motion of a trunk rotating to the left around the first axis. The right turn phase represents a motion of the trunk rotating to the right around the first axis. By the trunk rotating around the first axis, a pelvis rotates around the first axis with the motion of the trunk.

FIG. 6(b) illustrates moving states of abdominal muscles. When the turn phase is the left turn phase, left-side abdominal muscles contract, and right-side abdominal muscles stretch. When the turn phase changes from the left turn phase to the right turn phase, the left-side abdominal muscles contract most in the twisting motion, and the right-side abdominal muscles stretch most in the twisting motion. In this case, the left-side abdominal muscles act as agonist muscles, and the right-side abdominal muscles act as antagonist muscles.

When the turn phase is the right turn phase, the left-side abdominal muscles stretch, and the right-side abdominal muscles contract. When the turn phase changes from the right turn phase to the left turn phase, the left-side abdominal muscles stretch most in the twisting motion, and the right-side abdominal muscles contract most in the twisting motion. In this case, the right-side abdominal muscles act as agonist muscles, and the left-side abdominal muscles act as antagonist muscles.

FIG. 6(c) illustrates the value of angular velocity determined from results of detection by angular velocity sensor 51.

When user 100 forms twisting motion, angular velocity sensor 51 detects angular velocity around the first axis. In twisting motion, the trunk and the pelvis rotate in the same direction around the first axis. By considering this point, the stretching and contracting states of the abdominal muscles can be determined properly from results of detection by angular velocity sensor 51. When abdominal muscles on one of the right side and the left side stretch most, or when twisting motion is stopped, the angular velocity indicates substantially zero.

Examples of the thresholds referred to in the twisting motion mode are the following four types. The first is first threshold TP1, which is a threshold referred to for flowing current through right-side abdominal muscles. The second is second threshold TP2, which is a threshold referred to for stopping the flow of the current. The third is third threshold TM1, which is a threshold referred to for flowing current through left-side abdominal muscles. The fourth is fourth threshold TM2, which is a threshold referred to for stopping the flow of the current. The above-described thresholds are set by considering response delay between the output of a command signal from controller 30 to electrode pads 60 and the reflection of the command in the actual operation of electrode pads 60. Thus, thresholds TP1, TM1 referred to for flowing current and thresholds TP2, TM2 referred to for stopping current flow have different values.

Controller 30 compares the value of the angular velocity reflecting a result of detection by angular velocity sensor 51 with the thresholds to determine whether the value of the angular velocity falls within a predetermined range. For example, two types of predetermined ranges are set for the twisting motion mode. The first is a first predetermined range that is compared with the value of the angular velocity when the value of the angular velocity is changing from a negative peak to a positive peak. The second is a second predetermined range that is compared with the value of the angular velocity when the value of the angular velocity is changing from the positive peak to the negative peak. The first predetermined range and the second predetermined range are set across a positive region and a negative region as below, for example.

The first predetermined range is defined by first threshold TP1 and fourth threshold TM2. A range defined by first threshold TP1 and zero is a portion present in the positive region within the first predetermined range. A range defined by fourth threshold TM2 and zero is a portion present in the negative region within the first predetermined range.

The second predetermined range is defined by second threshold TP2 and third threshold TM1. A range defined by second threshold TP2 and zero is a portion present in the positive region within the second predetermined range. A range defined by third threshold TM1 and zero is a portion present in the negative region within the second predetermined range.

FIG. 6(d) illustrates current output forms.

When the value of the angular velocity changes from a magnitude of less than first threshold TP1 to a magnitude of more than or equal to first threshold TP1 at time t21, controller 30 causes right-side electrode pads 60 to output current, based on a result of comparison between the value of the angular velocity and first threshold TP1. In this case, since the value of the angular velocity is more than or equal to first threshold TP1, it is implied that right-side abdominal muscles are stretching as antagonist muscles. Thus, controller 30 causes right-side electrode pads 60 to output current so that electrical stimulation is provided to the right-side abdominal muscles.

When the value of the angular velocity changes from a magnitude of more than or equal to second threshold TP2 to a magnitude of less than second threshold TP2 at time t22, controller 30 stops the output of the current by right-side electrode pads 60, based on a result of comparison between the value of the angular velocity and second threshold TP2. In this case, since the value of the angular velocity is less than second threshold TP2, it is implied that the moving speed of the abdominal muscles is low, or the abdominal muscles are not moving. Thus, controller 30 stops the output of the current by right-side electrode pads 60 so that no electrical stimulation is provided to the abdominal muscles.

When the value of the angular velocity changes from a magnitude of more than or equal to third threshold TM1 to a magnitude of less than third threshold TM1 at time t23, controller 30 causes left-side electrode pads 60 to output current, based on a result of comparison between the value of the angular velocity and third threshold TM1. In this case, since the value of the angular velocity is less than third threshold TM1, it is implied that left-side abdominal muscles are stretching as antagonist muscles. Thus, controller 30 causes left-side electrode pads 60 to output current so that electrical stimulation is provided to the left-side abdominal muscles.

When the value of the angular velocity changes from a magnitude of less than fourth threshold TM2 to a magnitude of more than or equal to fourth threshold TM2 at time t24, controller 30 stops the output of the current by left-side electrode pads 60, based on a result of comparison between the value of the angular velocity and fourth threshold TM2. In this case, since the value of the angular velocity is more than or equal to fourth threshold TM2, it is implied that the moving speed of the abdominal muscles is low, or the abdominal muscles are not moving. Thus, controller 30 stops the output of the current by left-side electrode pads 60 so that no electrical stimulation is provided to the abdominal muscles.

In this manner, controller 30 stops the output of current by electrode pads 60 when the value of the angular velocity falls within the predetermined ranges, and causes corresponding electrode pads 60 to output current when the value of the angular velocity deviates from the predetermined ranges. When the twisting motion is continued at and after time t24, controller 30 repeatedly executes the same processing as the processing executed at times t21 to t24.

Figure 7:
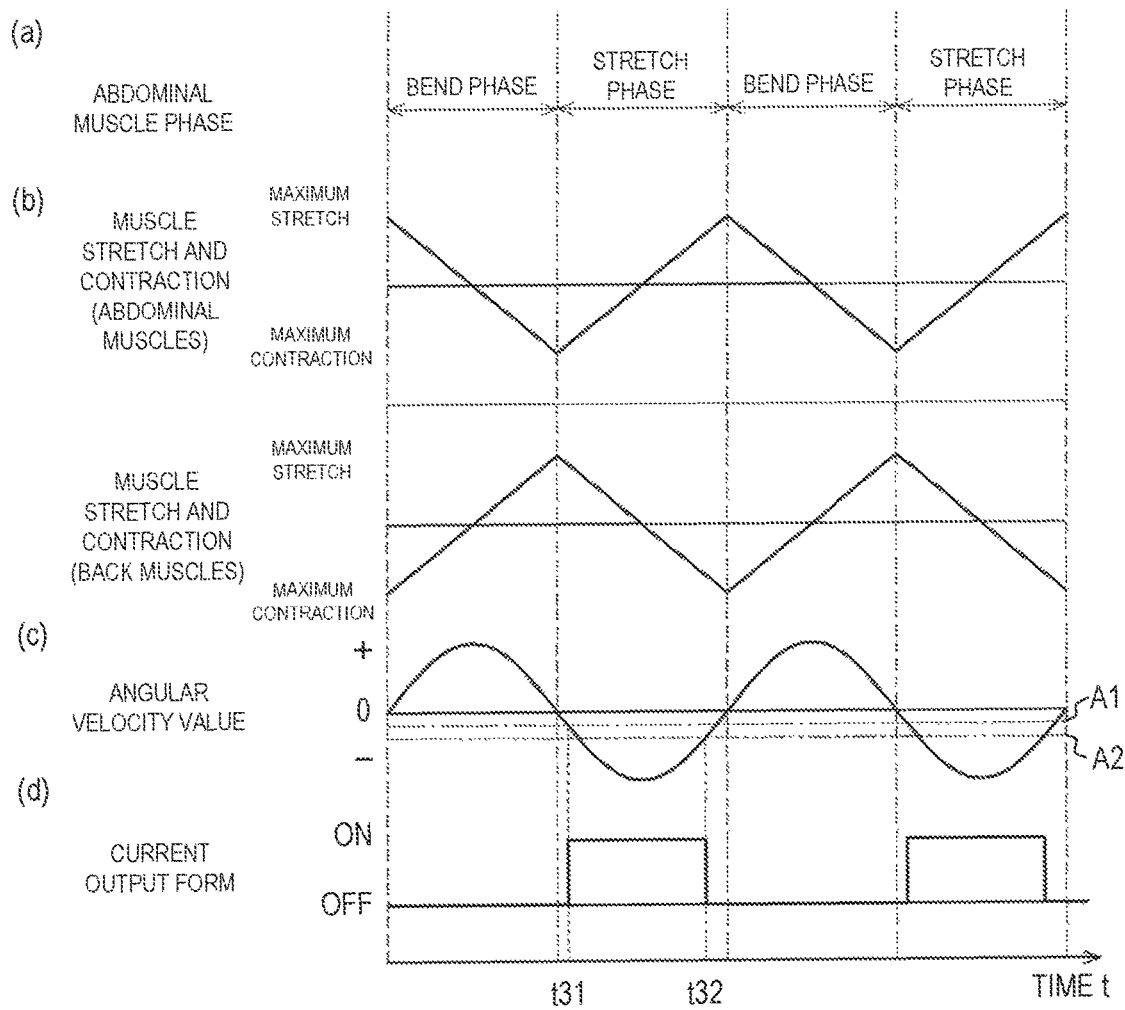
FIG. 7 is a time chart illustrating an example of changes in each item during bending motion of the electro-stimulator in FIG. 1 (in which (a) represents abdominal muscle phases, (b) represents muscle stretch and contraction, (c) represents an angular velocity value, and (d) represents a current output form).

With reference to FIG. 7, an example of the current output form in the bending motion mode will be described.

FIG. 7(a) illustrates an abdominal muscle phase, which is a phase related to motion of abdominal muscles in bending motion. An example of the bending motion is sit-ups, and its one cycle is divided into two abdominal muscle phases, a bend phase and a stretch phase. The bend phase represents a rising motion of an upper half of a body. The stretch phase represents a lying motion of the upper half of the body.

When the upper half of the body bends or stretches, a trunk rotates around the second axis. Here, a rotational direction of the trunk around the second axis is defined with reference to user 100 viewed from the left. Thus, when the upper half of the body bends, the upper half of the body rotates to the left around the second axis, and when the upper half of the body stretches, the upper half of the body rotates to the right around the second axis. By the upper half of the body rotating around the second axis, a pelvis rotates around the second axis with the motion of the upper half of the body.

FIG. 7(b) illustrates moving states of abdominal muscles. When the abdominal muscle phase is the bend phase, the abdominal muscles contract, and back muscles stretch. When the abdominal muscle phase changes from the bend phase to the stretch phase, the abdominal muscles contract most in the bending motion, and the back muscles stretch most in the bending motion. In this case, substantially all the abdominal muscles act as agonist muscles, and substantially all the back muscles act as antagonist muscles.

When the abdominal muscle phase is the stretch phase, the abdominal muscles stretch, and the back muscles contract. When the abdominal muscle phase changes from the stretch phase to the bend phase, the abdominal muscles stretch most in the bending motion, and the back muscles contract most in the bending motion. In this case, substantially all the back muscles act as agonist muscles, and substantially all the abdominal muscles act as antagonist muscles.

FIG. 7(c) illustrates the value of angular velocity determined from results of detection by angular velocity sensor 51.

When user 100 forms bending motion, angular velocity sensor 51 detects angular velocity around the second axis. For example, when the pelvis rotates to the left around the second axis, the angular velocity indicates positive values, and when the pelvis rotates to the right around the second axis, the angular velocity indicates negative values.

In bending motion, the trunk and the pelvis rotate in the same direction around the second axis. By considering this point, the stretching and contracting states of the abdominal muscles can be determined properly from results of detection by angular velocity sensor 51. When one side of the abdominal muscles and the back muscles stretch most, or when bending motion is stopped, the angular velocity indicates substantially zero.

Examples of the thresholds referred to in the bending motion mode are the following two types. The first is first threshold A1, which is a threshold referred to for flowing current through abdominal muscles. The second is second threshold A2, which is a threshold referred to for stopping the flow of the current. The above-described thresholds are set by considering response delay between the output of a command signal from controller 30 to electrode pads 60 and the reflection of the command in the actual operation of electrode pads 60. Thus, first threshold A1 referred to for flowing current and second threshold A2 referred to for stopping current flow have different values.

Controller 30 compares the value of the angular velocity reflecting a result of detection by angular velocity sensor 51 with the thresholds to determine whether the value of the angular velocity falls within a predetermined range. For example, two types of predetermined ranges are set for the bending motion mode. The first is a first predetermined range that is compared with the value of the angular velocity when the value of the angular velocity is changing from a negative peak to a positive peak. The second is a second predetermined range that is compared with the value of the angular velocity when the value of the angular velocity is changing from the positive peak to the negative peak. The first predetermined range and the second predetermined range are set across a positive region and a negative region as below, for example.

The first predetermined range is defined by second threshold A2, for example. A range more than or equal to zero is a portion present in the positive region within the first predetermined range. A range defined by second threshold A2 and zero is a portion present in the negative region within the first predetermined range.

The second predetermined range is defined by first threshold A1, for example. A range more than or equal to zero is a portion present in the positive region within the second predetermined range. A range defined by first threshold A1 and zero is a portion present in the negative region within the second predetermined range.

FIG. 7(d) illustrates a current output form.

When the value of the angular velocity changes from a magnitude of more than or equal to first threshold A1 to a magnitude of less than first threshold A1 at time t31, controller 30 causes all electrode pads 60 to output current, based on a result of comparison between the value of the angular velocity and first threshold A1. In this case, since the value of the angular velocity is less than first threshold A1, it is implied that all the abdominal muscles are stretching as antagonist muscles. Thus, controller 30 causes all electrode pads 60 to output current so that electrical stimulation is provided to all the abdominal muscles.

When the value of the angular velocity changes from a magnitude of less than second threshold A2 to a magnitude of more than or equal to second threshold A2 at time t32, controller 30 stops the output of the current by all electrode pads 60, based on a result of comparison between the value of the angular velocity and second threshold A2. In this case, since the value of the angular velocity is more than or equal to second threshold A2, it is implied that the moving speed of the abdominal muscles is low, or the abdominal muscles are not moving. Thus, controller 30 stops the output of the current by all electrode pads 60 so that no electrical stimulation is provided to the abdominal muscles.

In this manner, controller 30 stops the output of current by electrode pads 60 when the value of the angular velocity falls within the predetermined ranges, and causes corresponding electrode pads 60 to output current when the value of the angular velocity deviates from the predetermined ranges. When the bending motion is continued at and after time t32, controller 30 repeatedly executes the same processing as the processing executed at times t31 to t32.

Figure 8:
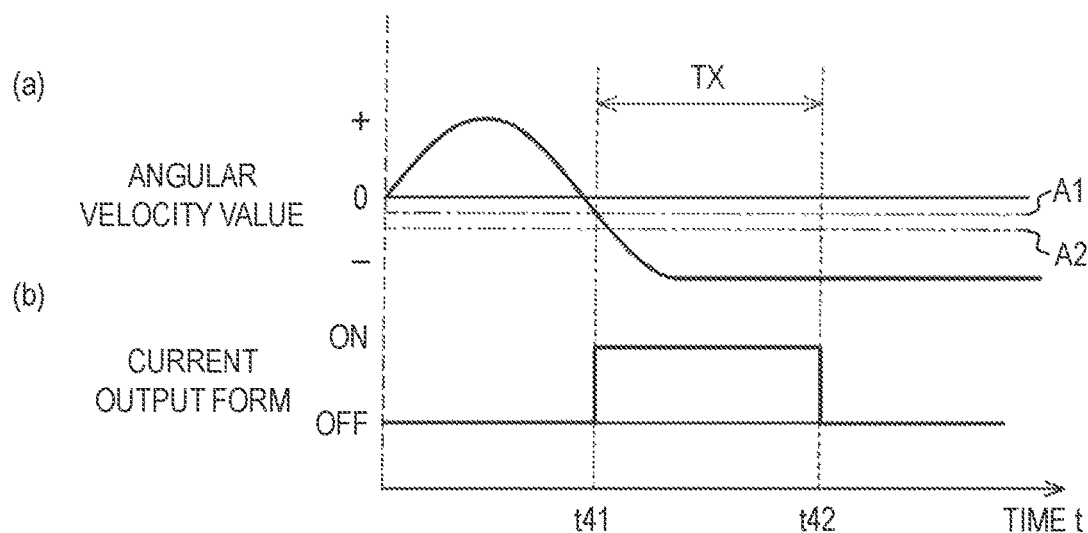
FIG. 8 is a time chart illustrating an example of an abnormal state during bending motion of the electro-stimulator in FIG. 1 (in which (a) represents an angular velocity value, and (b) represents a current output form).

FIG. 8 illustrates an abnormal state during bending motion.

To deal with an abnormality in output of angular velocity sensor 51, controller 30 determines a relationship between a duration, during which a state where the value of the angular velocity deviates from the predetermined ranges continues, and predetermined time TX. When the duration is more than or equal to predetermined time TX, it is implied that an abnormality has occurred in the output of angular velocity sensor 51. Thus, controller 30 stops the output of current by electrode pads 60, for example. Predetermined time TX is set for each motion mode, for example.

At time t41, controller 30 executes substantially the same processing as the processing executed at time t31 (see FIG. 7(*d*)) to cause all electrode pads 60 to output current. When the duration reaches predetermined time TX at time t42, controller 30 stops the output of the current by electrode pads 60. When walking motion, running motion, and twisting motion are formed, controller 30 controls electrode pads 60 based on the relationship between the duration and predetermined time TX in the same manner as described above.

Figure 9:
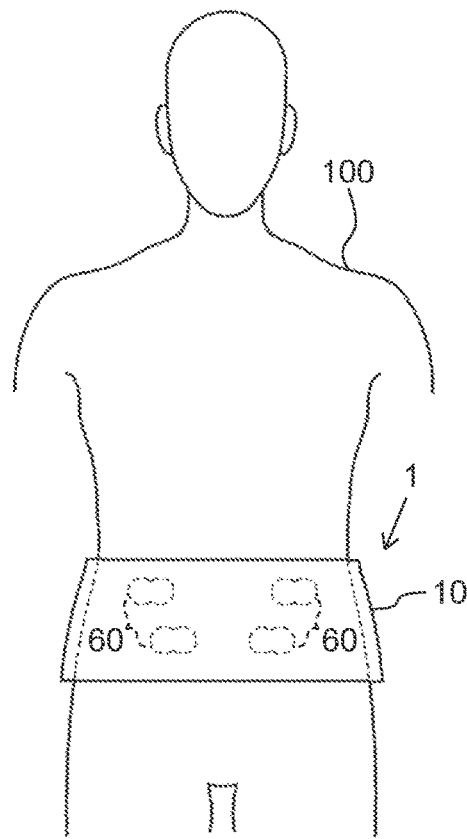
FIG. 9 is a front view illustrating an example of a used state of the electro-stimulator in FIG. 1.

With reference to FIG. 9, action of electro-stimulator 1 will be described.

Electro-stimulator 1 is used by user 100 in the following manner, for example. First, wearing part 10 is worn around the waist so that electrode pads 60 are disposed around the abdomen. Next, power switch 41 (see FIG. 4) is operated to switch the power from off to on. Next, mode selector 42 (see FIG. 4) is operated to select a motion mode corresponding to the type of motion of the body to be formed after that. Next, main body 20 (see FIG. 1) is housed in main body holder 12 (see FIG. 1). Then, user 100 forms the motion corresponding to the motion mode selected by mode selector 42.

As user 100 moves, information on the motion of the waist of user 100 is detected by angular velocity sensor 51 (see FIG. 1). Electrode pads 60 are controlled by controller 30 (see FIG. 1) according to results of the detection by angular velocity sensor 51 and the selected motion mode, so that current is output from electrode pads 60. Thus, the current flows through the abdomen, providing electrical stimulation to the abdomen, and training abdominal muscles properly.

Electro-stimulator 1 in the exemplary embodiment further provides the following effects.

(1) Motion of a waist causes abdominal muscles to move. Thus, the angular velocity of the waist has a correlation with the motion of the abdominal muscles. Based on this, electro-stimulator 1 detects the angular velocity of the waist by angular velocity sensor 51. Consequently, electrical stimulation according to the motion of the abdominal muscles is more likely to be provided to the abdomen.

(2) When electrical stimulation is provided to moving abdominal muscles, a higher training effect is likely to be obtained than when electrical stimulation is provided to motionless abdominal muscles. Based on this, electro-stimulator 1 detects angular velocity of the waist that accompanies motion of the body by angular velocity sensor 51. Consequently, electrical stimulation is more likely to be provided properly to the abdomen, according to the motion of the abdominal muscles.

(3) The mode of motion of the abdominal muscles differs according to the type of motion of the body. Based on this, electro-stimulator 1 detects angular velocity of the waist according to the type of motion of the body by angular velocity sensor 51. Consequently, electrical stimulation according to the mode of motion of the abdominal muscles is more likely to be provided to the abdomen. This further increases the possibility that the abdominal muscles are trained efficiently.

(4) The value of the angular velocity correlates with a degree of motion of the waist. Thus, by the predetermined ranges being preset in association with the motion of the waist, the relationship between the value of the angular velocity and the predetermined ranges implies the motion of the waist. According to an example, when the value of the angular velocity falls within the predetermined ranges, it is implied that the motion of the waist is small or the waist is not moving. When the abdominal muscles are not moving or the motion of the abdominal muscles is small, current passed from the electrode pad through an abdominal muscle may not train the abdominal muscle efficiently. Based on this, when the value of the angular velocity falls within the predetermined ranges, controller 30 of electro-stimulator 1 stops the output of current from electrode pads 60. This further increases the possibility that the abdominal muscles are trained efficiently.

(5) When the body moves for training, a state where the value of the angular velocity falls within the predetermined range, and the state where the value of the angular velocity deviates from the predetermined range are repeated substantially periodically. On the other hand, when an abnormality occurs in the output of angular velocity sensor 51, the state where the value of the angular velocity deviates from the predetermined ranges may continue. Thus, when the duration is more than or equal to predetermined time TX, it is highly likely that an abnormality in the output of the angular velocity sensor 51 has actually occurred. Based on this, when the duration is more than or equal to predetermined time TX, controller 30 of electro-stimulator 1 stops the output of current from electrode pads 60. This reduces a fear that the current is adjusted based on the value of the angular velocity that may not reflect the actual motion of the waist.

(6) The thresholds to be referred to for outputting current, and the thresholds to be referred to for stopping the output of current are set by considering response delay between the output of a command signal from controller 30 to electrode pads 60 and the reflection of the command in the actual operation of electrode pads 60. This reduces a fear of lowering the effect of training abdominal muscles due to lagging of the timing at which current is actually output from electrode pads 60 behind a desirable timing. Further, this reduces a fear of undesirable electrical stimulation being provided to the abdominal muscles due to lagging of the timing at which the output of current from electrode pads 60 is actually stopped behind a desirable timing.

(7) The positions of hooks 61 on electrode pad 60 are determined such that the center between two hooks 61 in the longitudinal direction of electrode pad 60 is longitudinally offset with respect to the longitudinal center of the electrode pad 60. Thus, when electrode pads 60 are attached to terminals 73, the distance between two electrode pads 60 in the longitudinal direction of pad holder 14 is changed, according to the direction in which the center between two hooks 61 is offset with respect to the longitudinal center of electrode pad 60. Thus, the positional relationships between electrode pads 60 and abdominal muscles are also changed. This configuration enables two-stage adjustment of the positional relationships between electrode pads 60 and abdominal muscles only by changing the direction of electrode pads 60 with respect to pad holder 14. Thus, the simple configuration improves the convenience of electro-stimulator 1.

(Modifications)

The description of the present exemplary embodiment is an illustration of a form that the electro-stimulator according to the present disclosure can take, and is not intended to limit the form. Other than the exemplary embodiment, the electro-stimulator according to the present disclosure can take, for example, modifications of the exemplary embodiment described below, and forms that combine at least two modifications consistent with each other.

The form of controlling electrode pads 60 by controller 30 based on the duration is a matter selected as desired. For example, when the duration is more than or equal to predetermined time TX, controller 30 makes the current output from electrode pads 60 smaller than current to be output when the duration is less than predetermined time TX.

The form of controlling electrode pads 60 by controller 30 based on the value of the angular velocity is a matter selected as desired. For example, when the value of the angular velocity falls within the predetermined ranges, controller 30 makes the current output from electrode pads 60 smaller than current to be output when the value of the angular velocity deviates from the predetermined ranges.

Details of modes selectable by mode selector 42 are matters selected as desired. For example, one or two of the walking motion mode, the running motion mode, the twisting motion mode, and the bending motion mode are omitted from mode selector 42. For another example, in addition to the above-described modes, a different mode is added to mode selector 42. An example of the different mode is a relax mode, which is a mode suitable for a case where a user forms a resting state. When the relax mode is selected, controller 30 causes electrode pads 60 to output weak current with a steady rhythm. Thus, soft electrical stimulation is provided to the abdomen.

Electro-stimulator 1 in a modification omits mode selector 42 from operating unit 40. In this modification, controller 30 determines the type of motion of a body based on a result of detection by angular velocity sensor 51, for example, and adjusts current output from electrode pads 60 based on the result.

Operating unit 40 in a modification further includes an output adjuster to be operated for adjusting a level of output of electrical stimulation. In this modification, controller 30 adjusts current output from electrode pads 60 according to an operation position of the output adjuster set by user 100.

Electro-stimulator 1 in a modification includes, in place of angular velocity sensor 51, a goniometer that detects information on motion of a waist.

Electro-stimulator 1 in a modification includes, in addition to angular velocity sensor 51, one or a plurality of different sensors that detect information on motion of a waist. An example of the different sensors is an acceleration sensor.

A relationship between a sign of the value of the angular velocity and a rotational direction of a body is a matter selected as desired. For example, when a pelvis rotates to the right around the first axis or the second axis, the angular velocity indicates positive values, and when the pelvis rotates to the left around the first axis or the second axis, the angular velocity indicates negative values.

The form of controlling electrode pads 60 by controller 30 based on the relationship between the value of the angular velocity and the thresholds is a matter selected as desired. For example, controller 30 stores a threshold referred to for flowing current and a threshold referred to for stopping the flow of current as a single threshold. Then, controller 30 determines the timing to output current and the timing to stop the output of current, based on the relationship between the value of the angular velocity and the single threshold. In this case, one type of predetermined range defined by one or two thresholds is set for each motion mode.

The mounted positions of hooks 61 on electrode pad 60 are matters selected as desired. For example, the mounted positions of hooks 61 on electrode pad 60 are determined such that the center between two hooks 61 agrees with the longitudinal center of electrode pad 60.

Electro-stimulator 1 in a modification includes one to three electrode pads 60 or five or more electrode pads 60.

Electro-stimulator 1 in a modification omits pad holder 14 from wearing part 10. In this case, user 100 directly attaches electrode pads 60 to the abdomen, and wrap wearing part 10 over electrode pads 60.

Sensor holder 13 in a modification has a structure slidable in the longitudinal direction of belt 11. In this case, even when electro-stimulator 1 is used by two or more users 100 of different body types, by sliding sensor holder 13, angular velocity sensor 51 is disposed in a desirable position.

Electro-stimulator 1 in a modification omits main body holder 12 from wearing part 10. In this case, user 100 uses electro-stimulator 1, grasping main body 20, for example.

Electro-stimulator 1 in a modification has main body 20 and sensor case 50 formed integrally. This modification can omit main body holder 12 from wearing part 10.

The current output forms by controller 30 are matters selected as desired. For example, controller 30 has a current output form of providing electrical stimulation to agonist muscles instead of antagonist muscles.

Controller 30 in a modification further has a current output form for twist lunges, standing trunk twists, and the like, which are an example of the twisting motion.

Controller 30 in a modification has a current output form for crunch, which is another example of the bending motion, in place of or in addition to the current output form for sit-up, which is an example of the bending motion.

(Additional Remarks on Solution to Problem)

[Additional Remark 1] The electro-stimulator according to any one of claims 1 to 6, further including a pad holder that holds the electrode pad, and a sensor holder that holds the sensor, wherein the pad holder and the sensor holder are supported by the belt.

[Additional Remark 2] The electro-stimulator according to claim 5, wherein the predetermined range is set for each type of motion of the body.

[Additional Remark 3] The electro-stimulator according to claim 5 or additional remark 2, wherein the predetermined range includes a first predetermined range that is compared with the value of the angular velocity when the value of the angular velocity is changing from a negative peak to a positive peak, and a second predetermined range that is compared with the value of the angular velocity when the value of the angular velocity is changing from the positive peak to the negative peak.

[Additional Remark 4] The electro-stimulator according to claim 6, wherein the duration is set for each type of motion of the body.

INDUSTRIAL APPLICABILITY

This electro-stimulator can be used for training of parts of a body including abdominal muscles.

REFERENCE MARKS IN THE DRAWINGS

1: electro-stimulator
11: belt
30: controller
51: angular velocity sensor (sensor)
60: electrode pad
TX: predetermined time

The invention claimed is:

1. An electro-stimulator for providing electrical stimulation to a muscle,
the electro-stimulator comprising:
an electrode pad that outputs current to provide the electrical stimulation;
a sensor for detecting an angular velocity of a waist of a human body around an axis along a direction of at least a height of the human body;
a controller that adjusts magnitude of the current output from the electrode pad, based on the angular velocity detected by the sensor; and
a belt that is adapted to be worn by the waits and supports the electrode pad, the sensor, and the controller,
wherein the sensor is supported by the belt so as to be positioned at a side of the human body when the belt is worn on the waist so that the electrode pad is disposed on the abdominal muscle.

2. The electro-stimulator according to claim 1, wherein the sensor detects the angular velocity of the waist that accompanies motion of the human body.

3. The electro-stimulator according to claim 2, wherein the motion of the human body is one of walking motion, running motion, twisting motion, and bending motion.

4. The electro-stimulator according to claim 2, wherein the controller adjusts the magnitude of the current output from the electrode pad, based on a current output form set for each type of motion of the human body and the angular velocity detected by the sensor.

5. The electro-stimulator according to claim 4, wherein when a value of the angular velocity detected by the sensor falls within a predetermined range, the controller prevents the electrode pad from outputting current or makes the current output from the electrode pad smaller than current to be output when the value of the angular velocity deviates from the predetermined range.

6. The electro-stimulator according to claim 5, wherein when a duration, during which a state where the value of the angular velocity deviates from the predetermined range continues, is more than or equal to a predetermined time, the controller prevents the electrode pad from outputting current or makes the current output from the electrode pad smaller than current to be output when the duration is less than the predetermined time.

* * * * *